(12) United States Patent
Dupelle et al.

(10) Patent No.: US 7,797,043 B1
(45) Date of Patent: Sep. 14, 2010

(54) PULSE SENSORS

(75) Inventors: Michael R. Dupelle, N. Attleboro, MA (US); Paul F. Prew, S. Attleboro, MA (US); Sheldon S. White, Brookline, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 515 days.

(21) Appl. No.: 10/992,402

(22) Filed: Nov. 17, 2004

Related U.S. Application Data (63) Continuation of application No. 09/846,673, filed on May 1, 2001, now abandoned.

(51) Int. Cl.
*A61N 1/00* (2006.01)
(52) U.S. Cl. .......................................................... 607/5
(58) Field of Classification Search ...................... 606/5, 606/6, 72; 600/516, 450, 454; 607/5, 4, 607/6, 72
See application file for complete search history.

(56) References Cited

U.S. PATENT DOCUMENTS

| | | | | |
|---|---|---|---|---|
| 3,716,059 | A | * | 2/1973 | Welborn et al. ................ 607/4 |
| 3,903,873 | A | | 9/1975 | Royal et al. |
| 4,052,979 | A | | 10/1977 | Scherr et al. |
| 4,299,233 | A | | 11/1981 | Lemelson |
| 4,331,154 | A | | 5/1982 | Broadwater |
| 4,443,730 | A | | 4/1984 | Kitamura et al. |
| 4,722,347 | A | | 2/1988 | Abrams et al. |
| 4,911,167 | A | | 3/1990 | Corenman et al. |
| 5,086,776 | A | | 2/1992 | Fowler, Jr. et al. |
| 5,409,009 | A | | 4/1995 | Olson |
| 5,431,685 | A | | 7/1995 | Alt |
| 5,595,188 | A | | 1/1997 | Kassal |
| 5,645,571 | A | | 7/1997 | Olson et al. |
| 5,795,300 | A | | 8/1998 | Bryars |
| 5,807,267 | A | | 9/1998 | Bryars et al. |
| 5,807,268 | A | | 9/1998 | Reeves |
| 5,827,198 | A | | 10/1998 | Kassal |
| 5,885,222 | A | | 3/1999 | Kassal et al. |
| 5,913,829 | A | | 6/1999 | Reeves et al. |
| 5,967,995 | A | * | 10/1999 | Shusterman et al. ........ 600/516 |
| 5,991,661 | A | | 11/1999 | Park et al. |

(Continued)

FOREIGN PATENT DOCUMENTS

JP 4015038 1/1992

(Continued)

OTHER PUBLICATIONS

Kassal et al., "Polymer-Based Adherent Differential-Output Sensor for Cardiac Auscultation," Medical Electronics, vol. 25, No. 4, Issue 148, pp. 54-63 (Sep. 1994).

(Continued)

*Primary Examiner*—George Manuel
(74) *Attorney, Agent, or Firm*—Fish & Richardson P.C.

(57) ABSTRACT

A method of operating an automated external defibrillator, the method being implemented by circuitry and one or more processors of the defibrillator, comprising monitoring a pulse signal from the patient; monitoring an ECG signal from the patient; determining whether it is appropriate to deliver a defibrillation shock to the patient, the determination being based at least in part on the content of the ECG signal and on the content of the pulse signal.

26 Claims, 8 Drawing Sheets

U.S. PATENT DOCUMENTS

| | | | |
|---|---|---|---|
| 6,292,692 B1 * | 9/2001 | Skelton et al. | 607/5 |
| 6,298,267 B1 | 10/2001 | Rosborough et al. | |
| 6,304,773 B1 | 10/2001 | Taylor et al. | |
| 6,356,785 B1 | 3/2002 | Snyder et al. | |
| 6,440,082 B1 | 8/2002 | Joo et al. | |
| 6,487,442 B1 | 11/2002 | Wood | |
| 6,567,697 B1 | 5/2003 | Kroll et al. | |
| 6,575,914 B2 | 6/2003 | Rock et al. | |
| 6,591,135 B2 * | 7/2003 | Palmer et al. | 607/5 |
| 2001/0047140 A1 | 11/2001 | Freeman | |
| 2002/0165585 A1 | 11/2002 | Dupelle et al. | |
| 2002/0173725 A1 | 11/2002 | Rock et al. | |
| 2003/0060723 A1 | 3/2003 | Joo et al. | |
| 2004/0039420 A1 | 2/2004 | Jayne et al. | |

FOREIGN PATENT DOCUMENTS

| | | |
|---|---|---|
| JP | 4028344 | 1/1992 |
| JP | 4028345 | 1/1992 |
| JP | 5261071 | 10/1993 |
| JP | 7265272 | 10/1995 |
| WO | 98/26716 | 6/1988 |
| WO | 95/06525 | 3/1995 |
| WO | 01/22885 | 4/2001 |

OTHER PUBLICATIONS

Webster, John G., Medical Instrumentation, Application and Design, 3rd ed., New York, NY, John J. Wiley & Sons, Inc. 1998.

* cited by examiner

Piezoelectric sensor   $R_{termination}$   $C_{cable}$

PULSE SENSORS

CROSS-REFERENCE TO RELATED APPLICATIONS

This application is a continuation application of and claims priority to U.S. application Ser. No. 09/846,673, filed on May 1, 2001 now abandoned.

TECHNICAL FIELD

This invention relates to pulse sensors and methods of using pulse sensors in conjunction with defibrillators.

BACKGROUND

The pulse is a very important parameter that is used to aid users of automated external defibrillators in determining whether or not to administer a defibrillation shock to and/or to perform cardiopulmonary resuscitation (CPR) on a victim who appears to be in cardiac arrest. Such a victim may actually be in need of cardiac resuscitation (including defibrillation and/or CPR), or may be suffering from a condition for which such treatment would be unsuitable, e.g., a stroke, seizure, diabetic coma, or heat exhaustion. It is very important to the safety of the victim that the presence or absence of a pulse be determined quickly and accurately. However, it is often difficult for trained medical personnel to take a victim's pulse accurately in the field during a crisis situation, and may be impossible for a minimally trained or untrained lay rescuer to do so. In many cases, it will take the person assisting the victim a considerable time (on the order of one minute or more) to find the victim's pulse. If a pulse is not found, the caregiver is left unsure as to whether the victim does not have a pulse, or whether the caregiver simply cannot find the victim's pulse.

Another parameter that is used in determining whether to administer a defibrillation shock is an ECG analysis of the victim's heart rhythm that is provided by the automated external defibrillator. Based on the ECG analysis, many automated defibrillators will provide the user with a message indicating whether a shock should be administered (i.e., whether or not ventricular fibrillation is present).

Generally, the ECG analysis systems in most commercially available automated external defibrillators display only two options to the user: "Shock Advised" or "No Shock Advised." When "Shock Advised" is output, this means that the patient is in ventricular fibrillation or wide complex ventricular tachycardia above 150 BPM, conditions which are effectively treated by defibrillation. When "No Shock Advised" is output, this means that the patient's heart rhythm is not treatable by defibrillation therapy.

If the message indicates that a shock is not appropriate, this does not necessarily mean that the victim is not in danger. There are two ECG rhythms, generally referred to as asystole and pulseless electrical activity, which should not be treated with defibrillation (and thus will trigger a message not to shock) but nonetheless are extremely serious in that they suggest that the patient's heart rhythm has deteriorated beyond fibrillation (i.e., the patient is close to death). These conditions are treated by administering cardiopulmonary resuscitation (CPR), in an effort to provide blood flow to the heart and vital organs in the hope that with improved blood flow and oxygenation, the heart muscle will recover from its near death state and possibly begin to fibrillate again, thus making defibrillation treatment a viable option.

Thus, when a "No Shock Advised" analysis is output, the caregiver does not know whether this result is caused by a normal heart rhythm, an abnormal but perfusing heart rhythm (i.e., the patient was never in cardiac arrest or the last shock treatment returned the patient's heart rhythm to normal), or a grossly abnormal (non-perfusing) ECG rhythm requiring CPR treatment. Because of this uncertainty, the normal medical protocol when "No Shock Advised" is output is to check the patient for a pulse and if no pulse is detected to start CPR. If a pulse is detected, then the patient's heart is effectively pumping blood and neither CPR nor defibrillation is warranted. If the victim does not have a pulse, CPR should be started immediately; if a pulse is present, then CPR should not be administered. Because CPR, even if properly administered, can result in broken ribs or other injury to the victim, it is undesirable to administer CPR if it is not actually necessary. Thus, it is again vitally important that an accurate determination of the presence or absence of a pulse be made by the caregiver.

A similar situation of uncertainty occurs after the third defibrillation shock is delivered in the three-shock protocol recommended by the American Heart Association. In this case, if the patient's fibrillation has not been "cured" after delivery of three shocks, the caregiver is instructed to perform CPR on the patient. Because automated external defibrillators generally do not perform an ECG analysis immediately after the third shock, the caregiver does not know whether the third shock provided effective treatment. Therefore, the caregiver must determine whether the patient has a pulse in order to determine whether CPR is needed or whether the patient is out of danger.

SUMMARY

The inventors have found that pulse sensors used in conjunction with automated external defibrillator machines enable users of such machines to make a quick and accurate determination of the appropriate treatment (defibrillation, CPR, or no cardiac-related treatment) for a victim who appears to be suffering from cardiac arrest. Such sensors provide an accurate determination of the presence or absence a victim's pulse, thus significantly reducing the risk that an inappropriate and even dangerous treatment will be given erroneously to a victim. The accurate pulse determination thus provided relieves the uncertainty experienced by caregivers in the circumstances discussed above, and thus increases the likelihood of the patient receiving prompt, safe and effective treatment.

The inventors have also found that pulse sensors used with automated external defibrillators can be used to determine whether CPR is necessary, in the event that an automated defibrillator indicates that it is not appropriate to shock a victim who appears to be suffering from cardiac arrest.

The invention also features methods of using pulse sensors to measure the efficacy of CPR, when CPR is used in conjunction with or instead of defibrillation.

In one aspect, the invention features a method of operating an automated external defibrillator, the method being implemented by circuitry and one or more processors of the defibrillator, comprising monitoring a pulse signal from the patient, monitoring an ECG signal from the patient, and determining whether it is appropriate to deliver a defibrillation shock to the patient, the determination being based at least in part on the content of the ECG signal and on the content of the pulse signal.

Implementations may include one or more of the following features. The monitoring of a pulse signal may comprise receiving the pulse signal from a pulse sensor applied to the exterior of the patient. The monitoring of an ECG signal may comprise receiving the ECG signal from defibrillation electrodes applied to the chest of the patient. The invention may further comprise providing assistance in the delivery of CPR to the patient. The invention may further comprise determining whether it is appropriate to deliver a defibrillation shock or CPR or neither. The invention may further comprise providing a user interface to provide information and recommendations to a user of the defibrillator. The user interface may comprise a display. The pulse sensor may comprise a piezoelectric sensor configured to detect motion caused by blood moving through an artery of the patient. The invention may further comprise comparing the content of the pulse signal to the content of the ECG signal to determine whether the pulse and ECG are correlated. The comparison may comprise a determination of whether the R wave of the heart rhythm found in the ECG is synchronized with the pulse. The pulse sensor may detect a pulse in a carotid artery. The invention may further comprise determining from the content of the pulse signal and the content of the ECG signal that the patient does not appear to be in cardiac arrest, and using the user interface to inform the user of that determination. The invention may further comprise determining from the content of the pulse signal and the content of the ECG signal that the patient should not be shocked, and using the user interface to inform the user of that determination. The invention may further comprise determining from the content of the pulse signal and the content of the ECG signal that the patient should not receive CPR, and using the user interface to inform the user of that determination. The invention may further comprise making an initial determination from the content of the pulse signal and the content of the ECG signal that the patient should not be shocked, using the user interface to inform the user of that initial determination, and following the initial determination continuing to analyze the content of the pulse signal and the ECG signal to make a second determination, based on the pulse becoming synchronized with the R-waves of the ECG, that the patient should be treated by administering a shock.

Other features and advantages of the invention will be apparent from the description and drawings, and from the claims.

DETAILED DESCRIPTION

Figure 1:
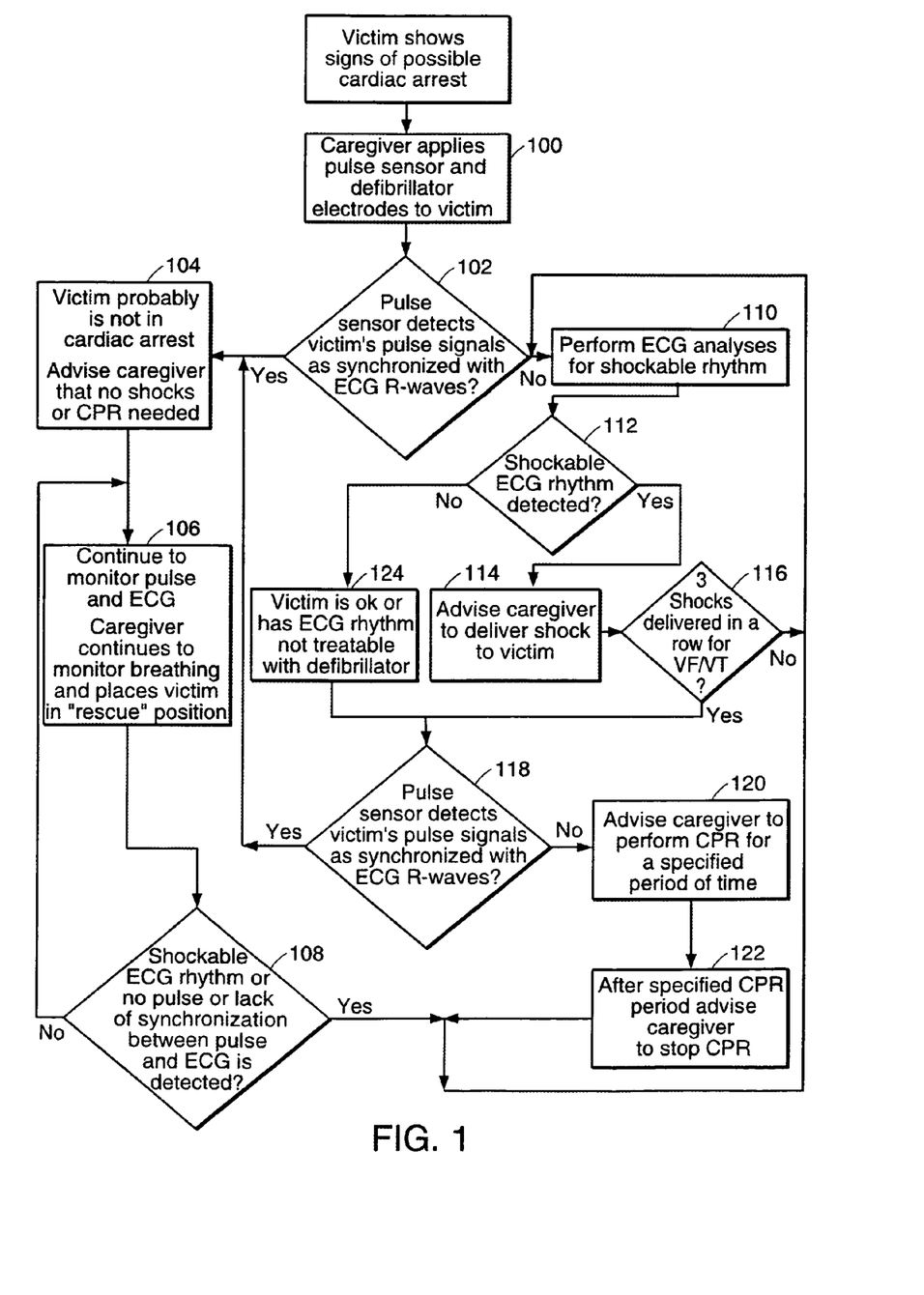
FIG. 1 is a flow diagram illustrating steps in a method according to one embodiment of the invention.
Figure 2:
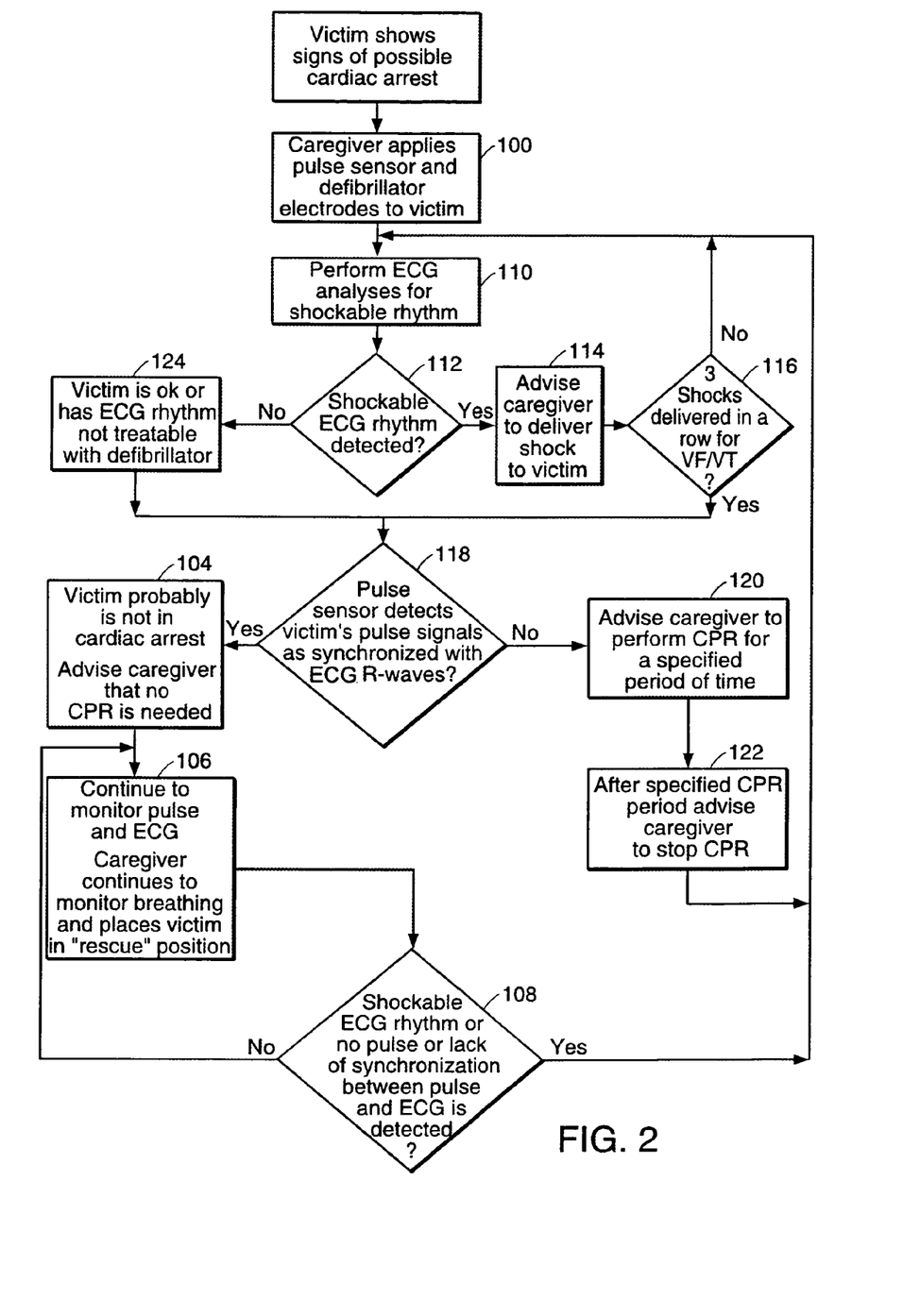
FIG. 2 is a flow diagram illustrating steps in a method according to an alternate embodiment of the invention.

FIGS. 1 and 2 show methods of using a pulse sensor and defibrillator to determine the appropriate treatment for a victim who appears to be suffering from cardiac arrest. Both methods utilize a pulse sensor, described in further detail below, and an automated defibrillator. The automated defibrillator includes (a) a pair of electrodes that are placed on the victim's chest, (b) instrumentation constructed to receive signals from the electrodes, monitor the victim's ECG based on the received signals, and deliver a shock to the electrodes, and (c) a display constructed to display information and recommendations to the caregiver. Suitable automated defibrillators are commercially available from Zoll Medical Corp., Burlington, Mass., e.g., M-Series Automated External Defibrillators. The instrumentation also includes the capability of comparing the R-wave of the heart rhythm monitored by the ECG to the victim's pulse to determine whether the two signals are synchronized. Together, the pulse sensor and defibrillator constitute a treatment system for victims who appear to be suffering from cardiac arrest.

FIG. 1 illustrates a method according to a first embodiment of the invention. In this method, the pulse sensor and defibrillator are used to control the initiation of ECG analysis and to advise a caregiver whether it is appropriate to administer a shock and/or CPR.

Figure 3:
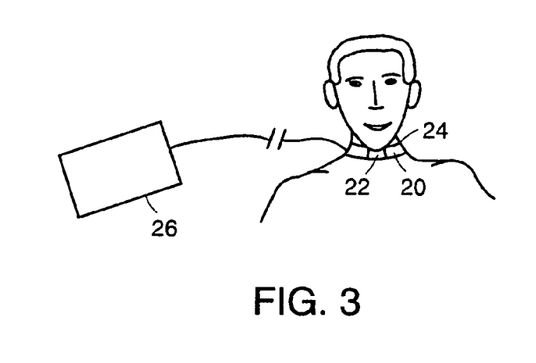
FIG. 3 is a diagrammatic view of a pulse sensor in use on a patient.

Referring to FIG. 1, when a victim shows signs of cardiac arrest, e.g., fainting, a caregiver applies a pulse sensor and the electrodes of a defibrillator to the victim (100). Generally, as shown in FIG. 3, the pulse sensor is applied by fastening an elastic strap 20 carrying the sensor element 22 around the victim's neck 24, so that the sensor element 22 is held in close contact with the victim's carotid artery by the elastic strap 20. The strap is fastened snugly but not tightly about the neck. Generally, to obtain an optimal signal the sensor should be placed on the left side of the neck orthogonal to and centered on the carotid artery. If desired, other locations on the patient's body where a pulse can normally be detected may be used instead of the neck. The neck is generally preferred since it is the measurement and sustenance of blood flow to the brain which is of ultimate importance and the carotid artery carrying this flow provides a strong signal if a pulse is present. The sensor element 22 is connected, e.g., by a coaxial cable, to instrumentation 26, which is preferably incorporated in the instrumentation of the defibrillator. The electrodes of the defibrillator are applied in a conventional manner.

Referring again to FIG. 1, the victim's pulse is detected and monitored by the pulse sensor, and the victim's heart rhythm is monitored by the ECG function of the defibrillator via the defibrillation pads. The instrumentation of the defibrillator determines whether the victim's pulse is correlated with the R-waves of the victim's heart rhythm (102). If the pulse and R-waves are synchronized, then a display on the defibrillator indicates to the caregiver that the victim does not appear to be in cardiac arrest, and that the victim should not be shocked or treated with CPR (104). In this case, the caregiver puts the victim in a "rescue" position, according to standard first aid protocol, and continues to monitor the victim's pulse and ECG (106) so as to observe if a change in synchronization, a loss of pulse signal or ventricular fibrillation should occur (108).

If the victim's pulse is or becomes unsynchronized with the R-waves, the defibrillator then performs an ECG analysis (110) to determine whether the victim's heart rhythm should be treated by administering an electrical shock, i.e., whether the victim is suffering from ventricular fibrillation or wide complex ventricular tachycardia (112).

If a shockable rhythm is detected, the display of the defibrillator advises the caregiver to administer a shock to the victim (114). The caregiver delivers a shock to the victim, and the defibrillator then performs another ECG analysis to determine whether a shockable rhythm is detected (110). As long as a shockable rhythm is detected, this process is repeated for three shocks (116). Once three shocks have been administered, the system checks again to see whether the victim's pulse is synchronized with the R-waves (118). If synchronization is not detected, then the display advises the caregiver to administer CPR for a specified period of time (120) and then to discontinue CPR (122). After CPR is discontinued, the ECG analysis (110) and following steps are repeated. If synchronization is detected, then a display on the defibrillator indicates to the caregiver that the victim does not appear to be in cardiac arrest, and that the victim should not be shocked or treated with CPR (104), and treatment proceeds as discussed above with reference to steps 106-108.

If a shockable rhythm is not detected, this indicates that either the victim is not suffering from cardiac arrest or that the victim has a condition that is not treatable by defibrillation (124). The system then checks again to see whether the victim's pulse is synchronized with the R-waves (118), and treatment proceeds, based on the results, as discussed above.

FIG. 2 illustrates an alternative method, in which the pulse sensor is used only to advise the caregiver whether it is appropriate to administer CPR. In this method, the ECG analysis is used alone to advise the caregiver whether it is appropriate to administer a defibrillation shock. This method may be used in cases in which checking the patient's pulse prior to applying the defibrillator electrodes is deemed to be unnecessary, e.g., the protocol that is currently recommended by the American Heart Association for lay caregivers. The other steps of the method shown in FIG. 2 are as described above with reference to FIG. 1.

Preferably, the pulse sensor is a piezoelectric polymer sensor. Piezoelectric sensors are, in their simplest form, capacitive electromechanical transducers that generate electrical charge in proportion to applied stress. The primary purpose of these sensors in the present invention is to generate an electrical signal that is proportional to the force caused by blood flow (pulse) in the area of the carotid artery or other areas of the body where a pulse could be detected. The sensors of the invention are not mechanically clamped at their periphery, and are primarily sensitive to longitudinal stress as opposed to a sound pressure wave front. Although the sensor material is somewhat sensitive to stress applied normal to its thickness and width, the sensor is designed to be most sensitive to stresses applied normal to its length (or "machine direction").

As blood flows through the carotid artery, or other area (either by normal heart action or as a result of CPR), the artery expands and exerts a small amount of stress on the sensor, which is in close contact with the exterior of the patient's neck, as discussed above. The stress induced in the sensor thus reflects changes in arterial blood flow.

Figure 4:
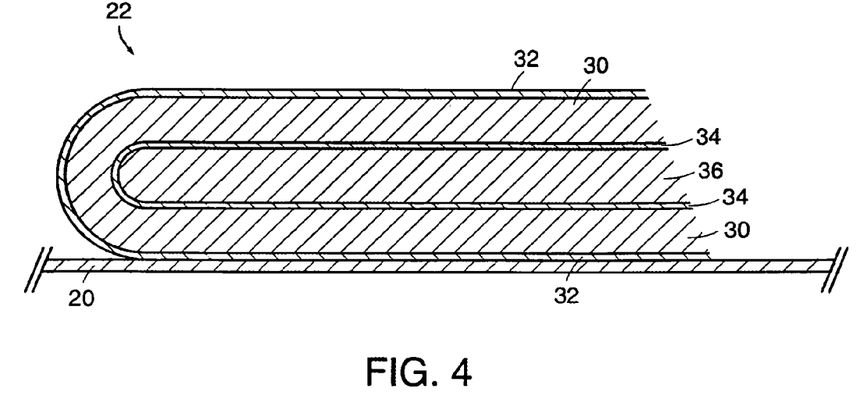
FIG. 4 is an enlarged diagrammatic cross-sectional view of a pulse sensor according to one embodiment of the invention.
Figure 4A:
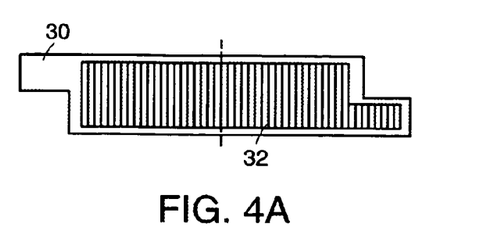
FIGS. 4A and 4B are unfolded and folded top views of the sensor element shown in FIG. 4.
Figure 4B:
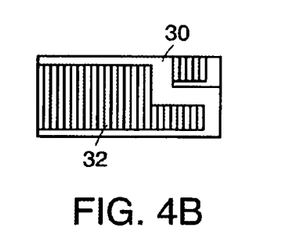
Figure 4C:
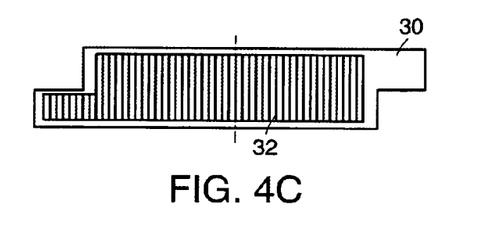
FIGS. 4C and 4D are unfolded and folded bottom views of the sensor element.
Figure 4D:
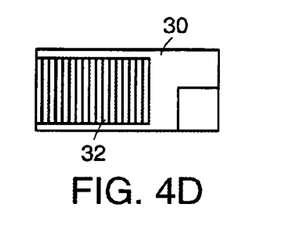

As shown in FIG. 4, the sensor includes a piezoelectric polymer film 30, a common metalization layer 32 and a signal metalization layer 34. Because piezoelectric sensors are generally of very high impedance, electrical interference is often problematic. To minimize electrical interference at the sensor surface, the sensor may be fabricated in a folded (self-shielding) manner, as shown in FIGS. 4, 4B and 4D, so that the common metalization layer 32 almost completely envelops the exterior of the sensor. The sensor is shown prior to folding in FIGS. 4A and 4C (top and bottom views, respectively) in which the dashed line indicates the line about which the sensor is folded. The sensor is held in its folded position by a layer of compliant adhesive 36 (FIG. 4). This shielding technique, in conjunction with coaxial cable connections, greatly minimizes interference created by undesirable stray electrical fields.

Figure 7:
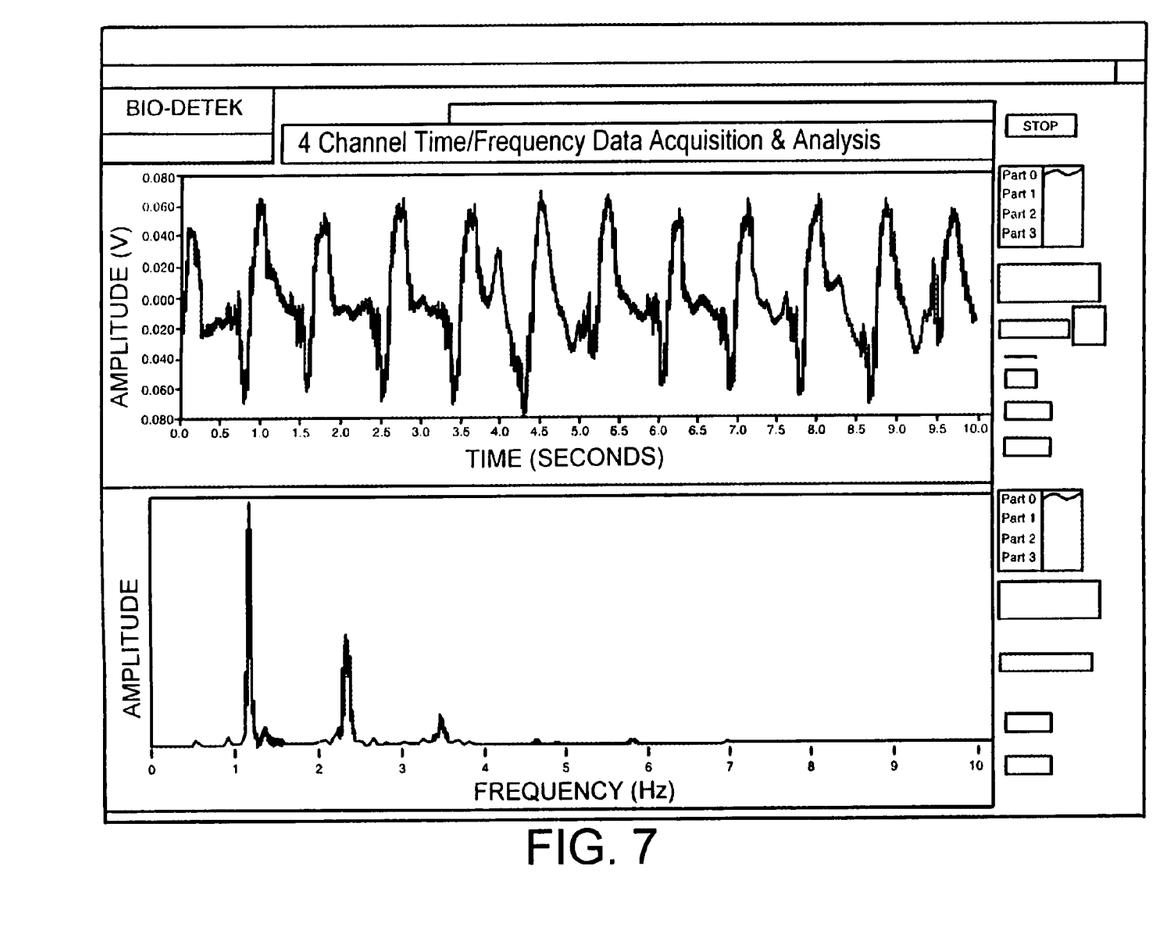
FIG. 7 is an example of a data acquisition scan performed using the pulse sensor of FIG. 4.

A data acquisition scan performed using the pulse sensor of FIG. 4 is shown in FIG. 7. The voltage signal level is approximately 100 my p-p with most of the energy being spectrally located at about 1.2 Hz, indicating a pulse rate of 72 beats/minute (bpm).

Suitable piezoelectric polymer films include polyvinylidine fluoride (PVDF) and co-polymers thereof. Such piezoelectric polymer films are commercially available, e.g., from Measurement Specialties, Inc. of Valley Forge, Pa. (e.g., Part No. 1-1004347-0). Preferably, the thickness of the polymer film is between about 0.001 and 0.005 inch.

A preferred sensor material is polarized piezoelectric polymer film sheet, about 28 micron (~0.001 inch) thick with a silver conductor printed on both sides for a total thickness of about 40 microns (~0.0015 inch). The sensor material may be approximately 5 inches in length and folded back upon itself with compliant adhesive, as shown in FIG. 4, to create a self-shielded sensor that is approximately 1.0 inch in width and 2.5 inches in length.

Figure 5:
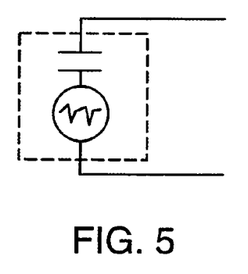
FIG. 5 is a schematic of the equivalent electrical circuit of the piezoelectric polymer film component of the pulse sensor.

An electrical signal is produced (as measured between the 'signal' and the 'shield' electrodes) when any stress is applied (especially in the longitudinal axis) to the sensor. The circuit shown in FIG. 5 consists of a voltage source in series with a capacitor. This circuit is acceptable for visualization and modeling of sensor elements of this type as long as the frequency is below ultrasonic range.

Figure 6:
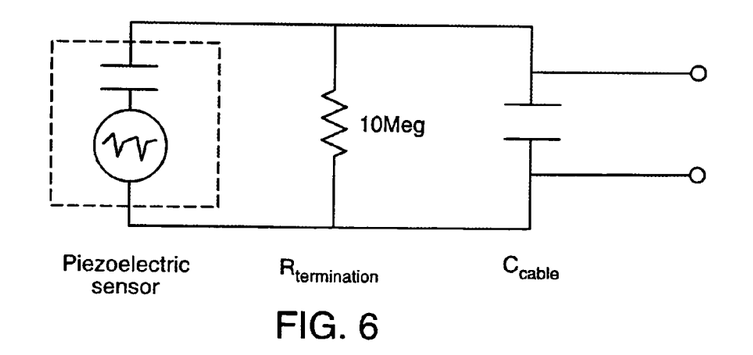
FIG. 6 is a circuit diagram of a complete pulse sensor assembly.

The capacitance exhibited by these sensors is approximately 10 nF and loss tangent is less than 0.02. Because the leakage is so low, it is generally necessary to eliminate long term buildup of charge (DC drift) on the electrodes due to triboelectric, pyroelectric or other phenomena especially when the sensor element is to be connected to a high (>10 meg ohm) impedance instrument. Eliminating this undesirable DC drift (charge buildup) is accomplished (at the expense of low frequency response) by placing a 'termination' resistor (10 Meg ohm) across (in parallel with) the sensor, as shown in FIG. 6. The termination resistor allows charge to bleed off from the sensor thus eliminating long-term voltage drift. The loss of low frequency response does not generally pose a problem, as it is typically preferable to minimize low frequency (<1 Hz) response so as to attenuate signals due to breathing or other slow artifacts.

FIG. 6 also shows the capacitance associated with the cable, which is used to connect the sensor to the instrumentation or other apparatus. The capacitance of the connecting cable appears in parallel with the capacitance of the sensor. This should not significantly impair the operation of the sensor as long as the cable capacitance is not appreciably large as compared to the capacitance of the sensor. If the sensor were operated in the 'current' mode (connected to a transimpedance amplifier, as shown in FIG. 13, or a charge amplifier, as shown in FIG. 14) the effect of the cable capacitance on the entire sensor system operation would be eliminated since there would be no appreciable voltage for the cable capacitance to charge to.

Figure 13:
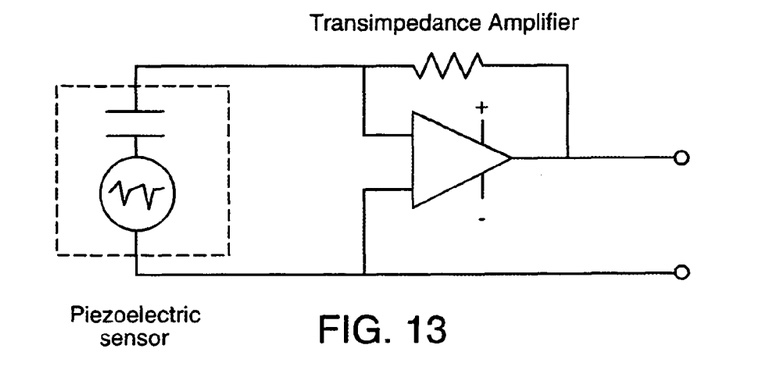
FIG. 13 is a schematic representation of a piezoelectric polymer film sensor element with a transimpedance (current to voltage converter) amplifier.
Figure 14:
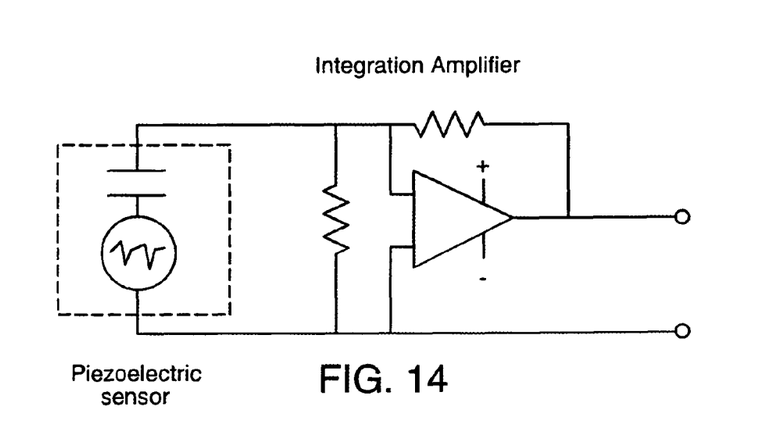
FIG. 14 is a schematic representation of a piezoelectric polymer film sensor element with an integrating amplifier (charge amplifier).
Figure 15:
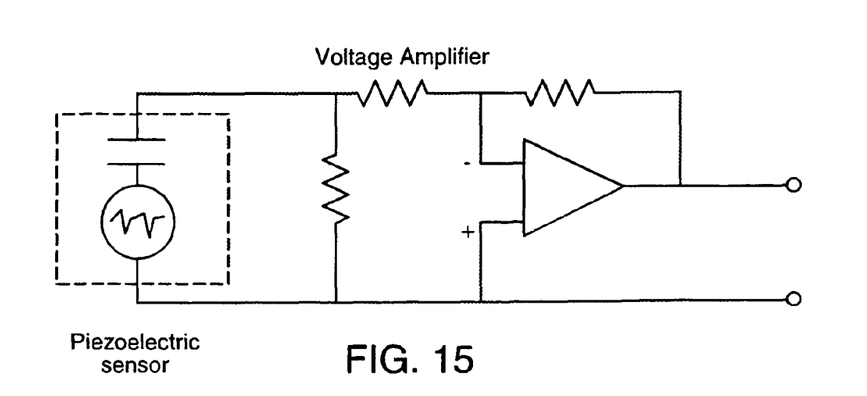
FIG. 15 is a schematic representation of a piezoelectric polymer film sensor element with a voltage amplifier.

The sensor electronics shown in FIGS. 13-15 may be integrated onto the sensor, or may be connected as a remote sensing instrument.

Other embodiments are within the scope of the following claims.

Figure 8:
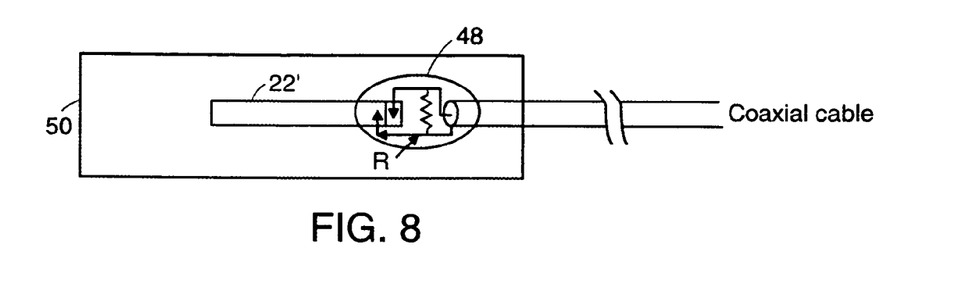
FIG. 8 is a diagrammatic representation of a pulse sensor according to an alternate embodiment of the invention.
Figure 9:
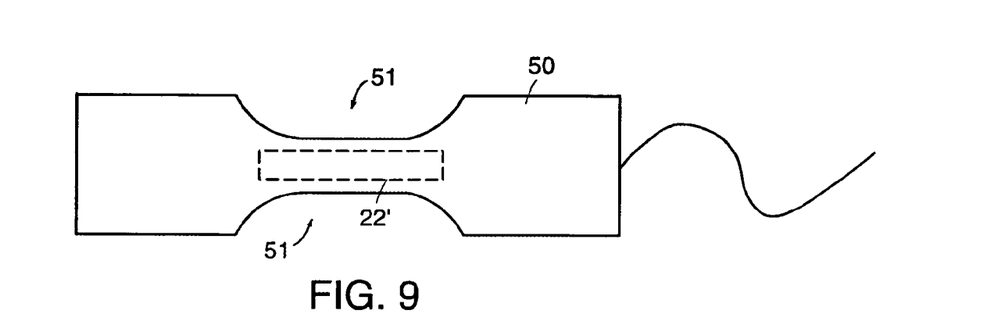
FIG. 9 is a diagrammatic representation of a sculpted sensor with enhanced sensitivity.

In alternative embodiments, a piezoelectric polymer sensor element 22' may be bonded to the surface of a compliant thickness member, e.g., a foam pad 50 as shown in FIGS. 8 and 9, to form a sensor assembly. A coaxial cable and terminating resistor are affixed to the foam pad and electrically connected to the sensor element. An epoxy 48 is applied to the resistor/cable/sensor area for protection. This sensor is designed to be most sensitive to forces which are normal to the length of the sensor. If desired, a second foam pad (not shown) may be adhered over the resistor/cable/sensor area. The foam pad is preferably about 1 to 2 mm thick, more preferably about 1.5 mm.

As shown in FIG. 9, if desired the foam pad 50 may be contoured in regions 51 to enhance signal sensitivity by allowing more stress to be felt by the sensor element 22.

Figure 10:
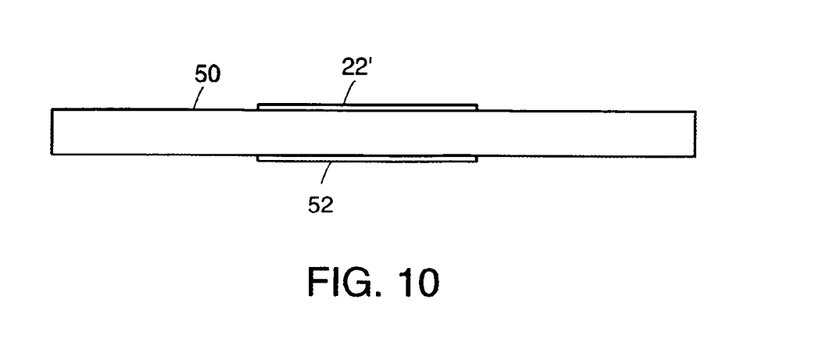
FIG. 10 is a side view of a piezoelectric polymer film sensor element with neutral plane inducer for optimized sensing of bending moments of the thickness member.

As shown in FIG. 10, the piezoelectric sensor may also be bonded to the surface of a neutral plane inducer 52, i.e., a compliant but non-stretchable member that converts any flexure in the assembly into a tensile or compressive motion normal to the sensor's length. Piezoelectric polymer sensors may be bonded to both opposing surfaces of a foam pad (not shown). Because any flexure in this assembly will cause tensile force in one sensor while simultaneously causing compressive force in the other sensor, the combined electrical signal will be differential in nature with advantages in increased sensitivity and improved common mode rejection of unwanted signals such as noise or pyroelectric response due to temperature transients.

Figure 11:
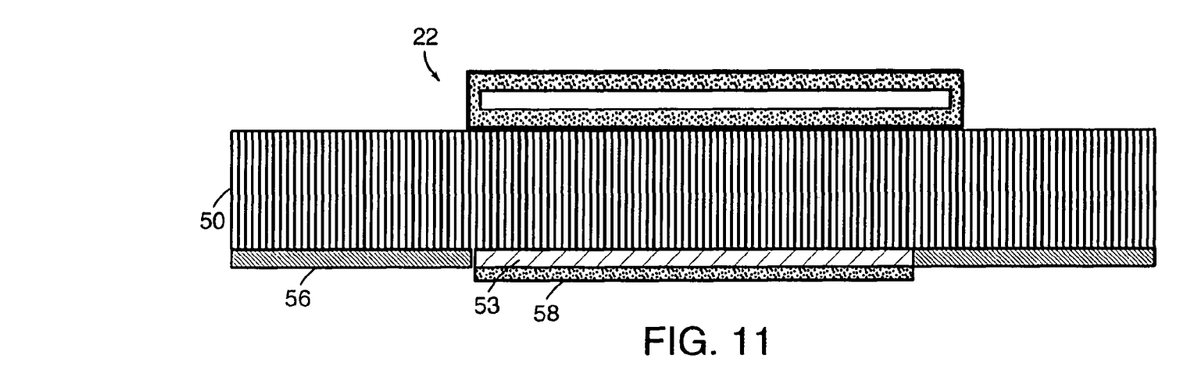
FIG. 11 is a cross sectional diagram of a piezoelectric polymer film pulse detector integrated into the fabrication of a defibrillator pad.

As shown in FIG. 11, the sensor element 22 (shown in FIG. 4 and described above) and foam pad 50 may be bonded to a defibrillator electrode 53, so that the sensor element may be attached to the chest as part of the defibrillator electrode. The defibrillator electrode includes a pressure-sensitive adhesive 56 and a conductive hydrogel 58, as is well known in the defibrillator field.

Figure 12:
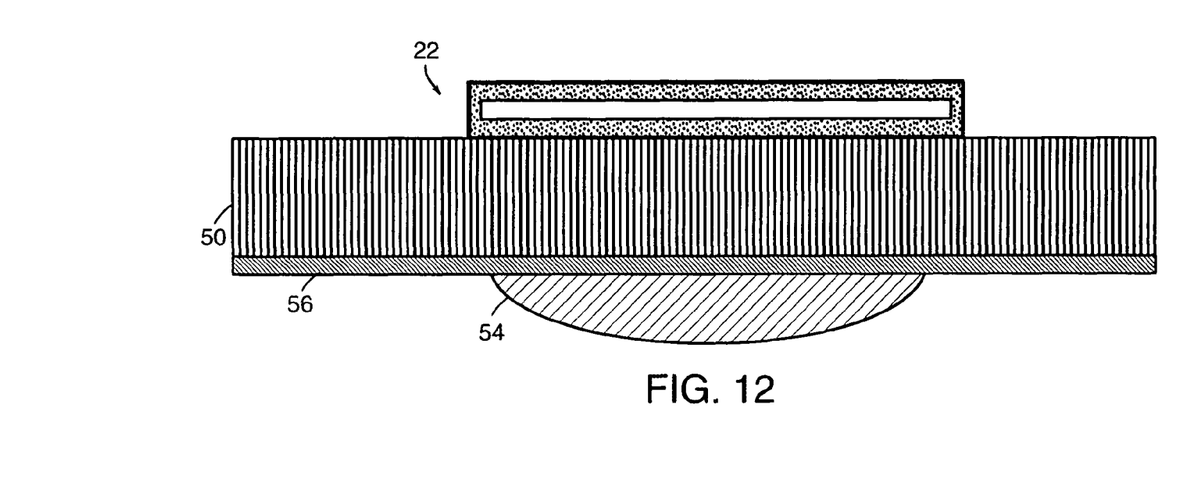
FIG. 12 is a cross sectional diagram of a piezoelectric polymer film pulse detector for use in a slightly concave body area such as that encountered in the area of the neck at the carotid artery.

As shown in FIG. 12, a stiff low mass object 54 may be bonded to the adhesive side of the foam pad to aid in making intimate contact with the carotid artery in cases where there are areas of depression in the neck surface.

The pulse sensor assembly may be used anywhere on the human body that a pulse can be detected, e.g., the neck, chest, wrist, arm or ankle. The unamplified voltage signal level output from the sensor should be in the approximate tenths of a volt range when properly affixed to an area of the body that exhibits a moderate pulse strength. The pulse sensor may be attached in a different manner, e.g., by a clip, as a patch, or using a suction device.

Small surface mount type electrical components such as operational amplifiers, resistors and capacitors may be integrated onto the sensor element and used to amplify the signal, provide noise immunity, mitigate the effects of cabling (parasitic capacitance and/or equivalent series resistance), filter certain frequencies, integrate the sensor electrical charge over time, double integrate the sensor electrical charge over time, scale and/or offset signal output, or otherwise accomplish signal conditioning functions for the electrical signals produced by the sensor element.

While automated defibrillators have been discussed above, the pulse sensor may be used in conjunction with a non-automated defibrillator. In this case the pulse sensor would be used by a trained caregiver as an aid in determining the proper course of treatment. The caregiver would observe displayed pulse and ECG signals and perform an independent analysis to determine the proper mode of treatment.

While the step of determining whether the patient's pulse signal and R-wave are synchronized is used in the methods described above, in many cases this step is not necessary. This step is a signal processing technique that is sometimes used to improve performance when one or both of the signals are contaminated with artifacts. Other suitable techniques include autocorrelation processing, matched filter processing, and other pattern recognition schemes. In some cases, e.g., if the signals are relatively uncontaminated, none of these techniques are required.

What is claimed is:

1. An external defibrillator, comprising:
   circuitry for delivering a defibrillation pulse to defibrillation electrodes applied to the chest of a patient;
   circuitry for monitoring a pulse signal from the patient, wherein the circuitry comprises circuitry for receiving the pulse signal from a piezoelectric sensor configured to detect motion caused by blood moving through an artery of the patient;
   circuitry for monitoring an ECG signal from the patient;
   one or more processors configured to determine whether it is appropriate to deliver a defibrillation shock to the patient, the determination being based at least in part on the content of the ECG signal and on the content of the pulse signal.

2. The external defibrillator of claim 1 wherein the circuitry for monitoring an ECG signal comprises circuitry for receiving the ECG signal from the defibrillation electrodes.

3. The external defibrillator of claim 1 wherein the one or more processors is further configured to assist in the delivery of CPR to the patient.

4. The external defibrillator of claim 3 wherein the one or more processors is further configured to determine whether it is appropriate to deliver a defibrillation shock or CPR or neither.

5. The external defibrillator of claim 1 further comprising a user interface to provide information and recommendations to a user of the defibrillator.

6. The external defibrillator of claim 5 wherein the user interface comprises a display.

7. The external defibrillator of claim 5 wherein the one or more processors is configured to determine from the content of the pulse signal and the content of the ECG signal that the patient does not appear to be in cardiac arrest, and to use the user interface to inform the user of that determination.

8. The external defibrillator of claim 5 wherein the one or more processors is configured to determine from the content of the pulse signal and the content of the ECG signal that the patient should not be shocked, and to use the user interface to inform the user of that determination.

9. The external defibrillator of claim 5 wherein the one or more processors is configured to determine from the content of the pulse signal and the content of the ECG signal that the patient should not receive CPR, and to use the user interface to inform the user of that determination.

10. The external defibrillator of claim 5 wherein the one or more processors is configured to make an initial determination from the content of the pulse signal and the content of the ECG signal that the patient should not be shocked, and to use the user interface to inform the user of that initial determination, and following that initial determination to continue to analyze the content of the pulse signal and the ECG signal to make a second determination, based on the pulse becoming unsynchronized with the R-waves of the ECG, that the patient should be treated by administering a shock.

11. The external defibrillator of claim 1 wherein the one or more processors is further configured to perform a comparison of the content of the pulse signal to the content of the ECG signal to determine whether the pulse and ECG are correlated.

12. The external defibrillator of claim 11 wherein the comparison comprises a determination of whether the R wave of the heart rhythm found in the ECG is synchronized with the pulse.

13. The external defibrillator of claim 1 wherein the pulse sensor detects a pulse in a carotid artery.

14. A method of operating an automated external defibrillator, the method being implemented by circuitry and one or more processors of the defibrillator, comprising:
monitoring a pulse signal from the patient, wherein the monitoring is performed by receiving the pulse signal from a piezoelectric sensor configured to detect motion caused by blood moving through an artery of the patient;
monitoring an ECG signal from the patient;
determining whether it is appropriate to deliver a defibrillation shock to the patient, the determination being based at least in part on the content of the ECG signal and on the content of the pulse signal.

15. The method of claim 14 wherein the monitoring of an ECG signal comprises receiving the ECG signal from defibrillation electrodes applied to the chest of the patient.

16. The method of claim 14 further comprising providing assistance in the delivery of CPR to the patient.

17. The method of claim 16 further comprising determining whether it is appropriate to deliver a defibrillation shock or CPR or neither.

18. The method of claim 17 further comprising providing a user interface to provide information and recommendations to a user of the defibrillator.

19. The method of claim 18 wherein the user interface comprises a display.

20. The method of claim 18 further comprising determining from the content of the pulse signal and the content of the ECG signal that the patient does not appear to be in cardiac arrest, and using the user interface to inform the user of that determination.

21. The method of claim 18 further comprising determining from the content of the pulse signal and the content of the ECG signal that the patient should not be shocked, and using the user interface to inform the user of that determination.

22. The method of claim 18 further comprising determining from the content of the pulse signal and the content of the ECG signal that the patient should not receive CPR, and using the user interface to inform the user of that determination.

23. The method of claim 18 further comprising making an initial determination from the content of the pulse signal and the content of the ECG signal that the patient should not be shocked, using the user interface to inform the user of that initial determination, and following the initial determination continuing to analyze the content of the pulse signal and the ECG signal to make a second determination, based on the pulse becoming unsynchronized with the R-waves of the ECG, that the patient should be treated by administering a shock.

24. The method of claim 14 further comprising comparing the content of the pulse signal to the content of the ECG signal to determine whether the pulse and ECG are correlated.

25. The method of claim 24 wherein the comparison comprises a determination of whether the R wave of the heart rhythm found in the ECG is synchronized with the pulse.

26. The method of claim 14 wherein the pulse sensor detects a pulse in a carotid artery.

* * * * *